United States Patent

Naylor

[11] 4,361,561
[45] Nov. 30, 1982

[54] METHOD OF TREATMENT OF MANIC DEPRESSIVE ILLNESS

[75] Inventor: Graham J. Naylor, Lulgate, Lucklawhill, Balmullo, St. Andrews KY16 0BQ, Fife, Scotland

[73] Assignees: Graham John Naylor; Pamela Hilda Naylor, both of St. Andrews, Scotland

[21] Appl. No.: 304,665

[22] Filed: Sep. 22, 1981

[51] Int. Cl.$^3$ .............................................. A61K 31/54
[52] U.S. Cl. ................................................... 424/247
[58] Field of Search ........................................ 424/247

[56] References Cited

PUBLICATIONS

Chem. Abst. 93 (1980) 2284q.

Primary Examiner—Stanley J. Friedman
Attorney, Agent, or Firm—Murray & Whisenhunt

[57] ABSTRACT

This invention relates to a method of treatment and/or prophylaxis of manic depressive illness comprising the administration of a therapeutically or prophylactically effective dosage of a compound of formula I

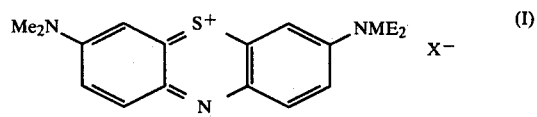

wherein X is a physiologically acceptable anion, or a bioprecursor thereof, to a patient suffering from manic depressive illness.

4 Claims, No Drawings

METHOD OF TREATMENT OF MANIC DEPRESSIVE ILLNESS

This invention relates to the treatment of manic depressive illness.

At the present time there is a significant incidence of manic depressive illness in society which results in considerable problems both for those members of society afflicted by this form of illness and for those others who come into contact with the sufferers.

It will be appreciated by those skilled in the art that many psychiatric disorders cannot be precisely and consistently defined so that similar or even identical illnesses are sometimes referred to by different names. For the avoidance of doubt therefore it should be noted that the expression "manic depressive illness" is intended to include one or more of those conditions referred to as: affective psychoses, manic depressive psychosis (or syndrome or reaction), manic psychosis, depressive psychoses, endogenous depression, melancholia, involutional melancholia, reactive or and psychogenic depressive psychosis (illness, syndrome or reaction), excitative nonorganic psychosis, hypomania, puerperal psychosis, puerperal manic depressive psychosis (illness, syndrome or reaction) unipolar depressive psychosis, bipolar depressive psychosis, and manic depressive psychosis including manic type, depressed type, circular type, and mixed type.

Present day methods for the control and management of this type of illness often involve substantial periods of hospitalization and are relatively expensive as well as not being particularly effective.

One known treatment comprises the regular administration of lithium. Although this method has been used to a significant extent at therapeutic concentrations it suffers from some significant adverse side-effects, notably tremor, nausea, polyuria, diarrhoea, oedema, possible irreversable renal damage, impairment of concentration and memory, and hypothyroidism. Also its therapeutic level is near to its toxic level and thus therapy must be monitored by regular (usually monthly) blood level estimations. Toxic effects include gross tremor, muscular inco-ordination, delirium, epileptic fits and death.

More recently the present inventor has found that ascorbic acid and EDTA (ethylene diamine tetracetic acid) are also useful in the short-term treatment of manic depressive illness. However these treatments appear to be less acceptable for the longer-term treatment which is often required. In the former case this is due to the significantly increased rate of ascorbic acid excretion after about three weeks of treatment at the relatively high dosage levels required thereby resulting in a significant reduction in effectiveness of the treatment. In the latter case this is due to the effects of EDTA on the removal of essential elements in the body which can result in the development of new illnesses of greater or lesser severity. In addition sudden withdrawal of ascorbic acid treatment may result in scurvy. Also significant numbers of patients develop diarrhoae during prolonged ascorbic acid treatment. In the case of EDTA this may be partially absorbed by the body and it is then potentially toxic, for example patients may suffer severe renal damage. Furthermore EDTA is teratogenic. In addition, when given orally EDTA often produces diarrhoea.

It is an object of the present invention to avoid or minimize one or more of the above disadvantages and in particular to provide a new method of treatment and/or prophylaxis of manic depressive illness.

The present invention provides a method of treatment and/or prophylaxis of manic depressive illness comprising the administration of a therapeutically or prophylactically effective dosage of a compound of Formula I

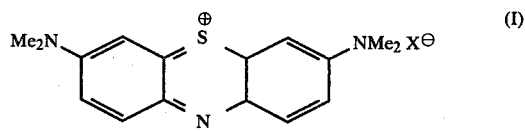

wherein X is a physiologically acceptable anion, or a bioprecursor thereof, to a patient suffering from manic depressive illness.

Preferably there is used a compound in which the anion is a halide anion especially chloride. In the latter case the compound of formula I is known as methylthionine chloride having the chemical formula $C_{16}H_{18}ClN_3S$. Other suitable anions which may be mentioned include sulphate, nitrate, citrate, carbonate and fumarate.

As well as being substantially free from the above-mentioned disadvantages of prior art methods to a greater or lesser extent, the present invention has additional advantages in that methylene blue appears to be more effective than ascorbic acid and is considerably cheaper.

In addition the present invention extends to the administration of a bioprecursor of a compound of formula I namely a compound which is readily converted in the human body upon administration into a said compound of formula I.

The preparation of compounds of formula I in particular of methylene chloride is well known from the literature. Particular desired salts or precursors can be readily produced by standard procedures such as metathetical reactions.

The inventor has also found that methylthionine chloride, usually referred to as methylene blue for convenience, has significant in vitro and in vivo activity in the reversal of Na-K ATPase inhibition caused in the body by, in particular, vanadate ions. It is believed that this is achieved by the reduction of vanadate ($V^{5+}$) ions to vanadyl ($V^{4+}$) ions. The inventor has also found that elevated vanadate ion levels in the body are associated with manic depressive illness. Whilst not restricting the scope of the present invention in any way it is believed by the inventor that the effectiveness of the method of the present invention is by means of the reversal of the Na-K ATPase inhibition in the body by vanadate ions.

The active compounds of the invention are usually administered in the form of a pharmaceutical formulation comprising the compound of formula I or bioprecursor thereof together with a pharmaceutically acceptable carrier therefor.

The carrier must be "acceptable" in the sense of being compatible with the other ingredients of the formulation and not deleterious to the patient. Such carriers may be solid, liquid or gaseous materials suitable for the purpose of administering the medicament by the desired route.

These pharmaceutical compositions may be administered orally or parenterally (including subcutaneous, intramuscular and intravenous injection) or as a suppository or pessary. In general the compositions are administered orally or parenterally. The words formulation and composition are used synonymously herein.

For parenteral administration the active compound may be presented in sterile solutions or suspensions in aqueous or oleaginous vehicles, which may also contain preservatives and material for rendering the solution or suspension isotonic with the blood of the patient. The formulations are conveniently presented in unit-dose or multi-dose sealed containers.

For oral administration the pharmaceutical compositions may be formulated as a draught in water or in a syrup, in capsules, cachets, boluses or tablets, as an aqueous or oleaginous solution of suspension or in suspension in a syrup, such suspensions optionally including suspending agents, or as an oil-in-water or water-in-oil emulsion. Flavouring, sweetening, preserving, thickening or emulsifying agents may also be included in the formulation.

Tablets may contain the active compound as a powder or granules optionally mixed with binders, lubricants, inert diluents or surface-active or dispersing agents and may be formed by compression or by moulding in inert liquid diluent. Such tablets may be scored and/or coated.

Capsules and cachets may contain the active compound alone or in admixture with one or more other ingredients. Capsules may also contain the active compound in aqueous or oleaginous solution suspension or emulsion optionally in association with other ingredients. For administration as a suppository or pessary the active compound may be presented in admixture with a suitable carrier such as cocoa butter and other material commonly used in the art, and are conveniently shaped by moulding. For administration in discrete unit dosage forms such as tablets, capsules, suppositories and pessaries as described above, the active compound is preferably present at from 1 mg to 300 mg, most preferably from 25 mg to 300 mg, per tablet, capsule, suppository or pessary.

All the above formulations may be produced by standard processes comprising bringing the active compound into association with one or more pharmaceutically acceptable carriers.

The required effective dosage of the compound of formula I will of course depend on various factors such as the activity of the individual compound, the depth, the severity of the illness, and the responsiveness of the individual patient to the treatment regimen used. In general though the compound of formula I will be administered at a dosage in the range of from 0.1 to 10 mg per kg body weight of the patient per day, preferably from 1 to 8 mg/kg. Advantageously the dosage is administered in two or more equal portions at approximately equal intervals.

Further preferred features of the invention will appear from the following example.

EXAMPLE 1

Two manic depressive patients with 7 week cycles who had been in hospital for several years and had failed to respond to lithium were treated with methylene blue. Patient 1, aged 28, had a 7 week cycle. Patient 2 was a 58 year old woman with a history of manic depressive psychosis for over 30 years and which had been regularly cyclic over the past two to three years. Severity ratings were made twice daily by nursing staff on a simple global rating scale (manic 1-3, normal, depression 1-3). The results have been expressed as percentage of total cycle time in each phase. Patient 1 had previously shown some response to a low vanadium diet, oral EDTA and large doses of ascorbic acid. This treatment was continued and for one cycle the patient received 100 mg methylene blue intravenously on four days per week. The following cycle she received no methylene blue and then received oral methylene blue 100 mg b.d. for one cycle. Patient 2 had received haloperidol 6 mg daily for several months. This was continued and for one cycle (7 weeks) she received oral methylene blue 100 mg b.d. A double blind procedure was impossible because methylene blue produces a blue urine (Patient 1 was also incontinent).

RESULTS

The results are shown in Table I. The percentage of time ill when on methylene blue in Patient 1 is shown compared with the time ill on the same medication but without methylene blue (i.e. the preceding 33 weeks and the 7 weeks between the methylene blue treatments). The results for the preceding 2 full years are also known. During the two periods on methylene blue, the time this patient was normal or only mildly ill increased and this change was predominantly reduction in the time spent depressed. The results of the 7 weeks treatment with methylene blue in Patient 2 are shown compared with the preceding 16 weeks during which she received the same medication apart from methylene blue, and with the same 7 weeks in the previous year. During the cycle on methylene blue the patient was dramatically improved, spending 59% of the time well compared with 12% and 13% when not on methylene blue. This was also clearly revealed in the days she spent out of hospital—13 days in the 7 weeks of methylene blue compared with 2 to 4 days without. This improvement was predominantly a reduction in time spent depressed but the clinical impression was that the manic phase was also ameliorated. The results in both patients were statistically significant by $X^2$ test.

TABLE I

Clinical results on cyclic patients. Results are presented as percentage of time in each phase of the cycle

| PATIENT 1 | | | | | | |
|---|---|---|---|---|---|---|
| | Year 1 | Year 2 | Preceding 33 weeks EDTA + Vit C | 7 week EDTA + Vit C + IV methylene blue | 7 week EDTA + Vit C | 7 week EDTA + Vit C + oral methylene blue |
| Normal or mildly ill | 49 | 41 | 64 | 84 | 56 | 77 |
| Severely depressed | 39 | 48 | 27 | 0 | 32 | 19 |
| Severely manic | 12 | 11 | 9 | 16 | 12 | 4 |

PATIENT 2

TABLE I-continued

| | 7 weeks (in preceding year, same dates) | 16 weeks preceding | 7 weeks of methylene blue |
|---|---|---|---|
| Normal or mildly ill | 12 | 13 | 59 |
| Severely depressed | 40 | 51 | 8 |
| Severely manic | 48 | 36 | 33 |
| Days out/week | 0.57 | 0.31 | 1.86 |

*Clinical results on cyclic patients. Results are presented as percentage of time in each phase of the cycle*

What is claimed is:

1. A method of treatment and/or prophylaxis of manic depressive illness comprising the administration of a therapeutically or prophylactically effective dosage of a compound of formula I

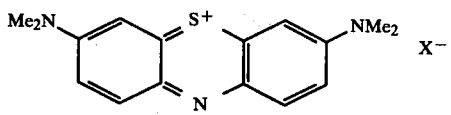

wherein X is a physiologically acceptable anion, or a bioprecursor thereof, to a patient suffering from manic depressive illness.

2. A method according to claim 1 wherein X is a halide anion.

3. A method according to claim 2 wherein the compound is methylthionine chloride.

4. A method according to claim 3 wherein methylthionine chloride is administered at a dosage rate of from 0.1 to 10 mg per kg bodyweight of the patient per day.

* * * * *